United States Patent [19]

Murakami et al.

[11] Patent Number: 6,048,713
[45] Date of Patent: Apr. 11, 2000

[54] *PSEUDOMONAS FLUORESCENS*

[75] Inventors: Koji Murakami; Akiko Kudo; Hideaki Yamada; Ken Kanzaki; Kenzo Okada, all of Ibaraki, Japan

[73] Assignee: Nisshin Flour Milling Co., Ltd., Tokyo, Japan

[21] Appl. No.: 08/827,120

[22] Filed: Mar. 27, 1997

[51] Int. Cl.$^7$ .............................. C12P 19/34; C12N 1/00; C12N 1/20
[52] U.S. Cl. .................... 435/91.2; 435/243; 435/252.34
[58] Field of Search .............................. 435/91.2, 252.34, 435/243

[56] References Cited

U.S. PATENT DOCUMENTS 4,900,348  2/1990  Hoitink ......................................... 71/6

OTHER PUBLICATIONS

K. Murakami et al., Biocontrol of Brown Patch Disease of Creeping Bentgrass and PGPR Activity by *Pseudomonas fluorescens* HP72, Preliminary Papers of the Phytopathological Society of Japan published on Apr. 1, 1996.

K. Murakami et al., Monitoring of Antagonistic Pseudomonas Strains in Field, Preliminary Papers of the Soil & Fertilizer Science Society of Japan published on Apr. 2, 1995.

*Primary Examiner*—Lisa B. Arthur
*Assistant Examiner*—Jehanne Souaya
*Attorney, Agent, or Firm*—Fish & Richardson P.C.

[57] ABSTRACT

A novel *Pseudomonas fluorescens* is disclosed which has an antagonist property against pathogenic fungi of the genera Pythium, Rhizoctonia, Sclerotinia and Gaeumannomyces and which has a DNA that forms a PCR product band at about 800 bp when replicated and amplified by PCR using a primer DNA having the base sequence of 5'-GGCAACTGCACAAGCGCCA (SEQ ID NO: 1) and a primer DNA having the base sequence of 5'-GCCAATCACGCCCTCAAGCT (SEQ ID NO: 2) and then electrophoresed on agarose gel. This microorganism can also promote the growth of plants. A material for controlling pathogenic fungi of plants, particularly, lawn grass, a plant growth promoting material and a compost comprising the microorganism are also disclosed.

12 Claims, No Drawings

PSEUDOMONAS FLUORESCENS

BACKGROUND OF THE INVENTION

1. Field of the Invention

The present invention relates to a novel *Pseudomonas fluorescens* bacterium and variants thereof, and a material for controlling a plant pathogenic fungus, a plant growth promoting material and a compost comprising the above bacterium. More specifically, the present invention relates to a *Pseudomonas fluorescens* bacterium having an antagonistic property against plant pathogenic fungi of the genera Pythium, Rhizoctonia, Sclerotinia and Gaeumannomyces, growing well in the rhizosphere of a plant to sufficiently reveal the antagonistic property against the pathogenic fungi and being able to promote the growth of the plant by promoting the elongation of the root system and leaves of the plant, and also relates to a material for controlling plant pathogenic fungi, a plant growth promoting material and a compost comprising the above microorganism.

2. Description of the Prior Art

Lawn grass planted in golf courses and the like suffers a great damage from various kinds of lawn grass pathogenic fungi. Specifically, pythium red blight caused by *Pythium aphanidermatum*, spring dead spot caused by *Pythium vanterpooli*, brown patch caused by pathogenic fungi of the genus Rhizoctonia such as *Rhizoctonia solani*, dollar spot caused by pathogenic fungi of the genus Sclerotinia such as *Sclerotinia homoeocarpa*, take-all patch caused by pathogenic fungi of the genus Gaeumannomyces such as *Gaeumannomyces graminis* and the like may be cited for example.

As a means to control pathogenic fungi of plants such as lawn grass, application of drugs such as agricultural chemicals, selection of a variety resistant to pathogenic fungi and the like have been performed conventionally. In particular, application of drugs has been widely practiced. However, this method has caused various problems e.g., accumulation and remaining of drugs in human bodies and other organisms, stimulating smell, inflow and infiltration of drugs into rivers and underground water, destruction and pollution of natural environments such as destruction of ecosystems; thus, this method has become a big social problem.

In the method of selecting a variety resistant to pathogenic fungi, the variety of a plant to be grown is restricted and very often the growth environments and soil are not necessarily suitable for that variety.

Also, compound fertilizers have been used abundantly to promote the growth of plants. However, although compound fertilizers act quickly, they cause problems such as poor growth or withering due to inappropriate concentration of the fertilizer, infertilization of soil due to repeated application, environmental pollution and the like. A plant growth promoting material which does not cause such problems and which can replace compound fertilizers is needed.

SUMMARY OF THE INVENTION

Under the above-mentioned circumstances, the present inventors have searched for a useful microorganism having an antagonistic property against pathogenic fungi of plants (particularly, lawn grass) for a long time from the view point that it is appropriate to control pathogenic fungi of plants such as lawn grass with a microorganism having an antagonistic property against them instead of controlling them with drugs. As a result of the screening of an extremely large number of fungi and bacteria for the presence of an antagonistic property, it has been found that ray fungi of the genus Streptomyces such as *Streptomyces heimi*, *Streptomyces flaveolus*, *Streptomyces misionensis* and *Streptomyces fumanus* and the bacterium *Shewanella putrefaciens* have a highly antagonistic property especially against lawn grass pathogenic fungi such as *Pythium aphanidermatum* causing pythium red blight and *Pythium vanterpooli* causing spring dead spot and are able to control those diseases of lawn grass effectively. Thus, the inventors have previously filed a patent application for this finding (Japanese Unexamined Patent Publication No. 6-107512).

As a result of further investigation into a microorganism having an antagonistic property against lawn grass pathogenic fungi, the present inventors have found a strain among bacteria belonging to *Pseudomonas fluorescens* which grows well in the rhizosphere of a plant, particularly, lawn grass and which is able to control plant pathogenic fungi effectively.

Then, the bacteriological properties of the above *Pseudomonas fluorescens* bacterium found by the present inventors which grows well in the rhizosphere of a plant have been examined in detail. As a result, it has been found that while known *Pseudomonas fluorescens* bacteria do not produce any PCR (polymerase chain reaction) product which forms a band at about 800 bp when their DNAs have been replicated and amplified by PCR using a primer DNA having the base sequence of 5'-GGCAACTGCACAAGCGCCA shown in SEQ ID NO: 1 and a primer DNA having the base sequence of 5'-GCCAATCACGCCCTCAAGCT shown in SEQ ID NO: 2 and then electrophoresed on agarose gel, the above-mentioned *Pseudomonas fluorescens* strain found by the present inventors has a DNA that forms a PCR product band at about 800 bp when subjected to PCR under the same conditions and then electrophoresed on agarose gel. Thus, the strain has been found to be a novel strain different from known *Pseudomonas fluorescens* strains.

The present inventors have also investigated for a long time into a fertilizer and a plant growth promoting material which are safe and free from the problem of injury by continuous cropping or the infertilization of soil and which can replace conventional compound fertilizers. From such points of view, the properties of the novel *Pseudomonas fluorescens* strain found by the present inventors have been examined in detail. As a result, it has been found that the novel *Pseudomonas fluorescens* strain is effective for the elongation of the root system of a plant such as lawn grass, especially effective for the elongation of the root system at the early stage of growth and further effective for the elongation of leaves and the like of a plant. Thus, the novel strain has been found to have a plant growth promoting action. Based on these findings, the present invention has been completed.

The present invention relates to a *Pseudomonas fluorescens* having an antagonistic property against plant pathogenic fungi and having a DNA portion that forms a PCR product band at about 800 bp when replicated and amplified by PCR using a primer DNA having the base sequence of 5'-GGCAACTGCACAAGCGCCA shown in SEQ ID NO: 1 and a primer DNA having the base sequence of 5'-GCCAATCACGCCCTCAAGCT shown in SEQ ID NO: 2 and then electrophoresed on agarose gel. As a specific example of such a strain, *Pseudomonas fluorescens* HP-72 may be given.

The present invention also relates to variants of the above-mentioned *Pseudomonas fluorescens* HP-72, i.e.

*Pseudomonas fluorescens* HP-72-B13 in which the antagonistic property against plant pathogenic fungi has been enhanced compared to the parent strain HP-72, and *Pseudomonas fluorescens* HP-72-Br3 and *Pseudomonas fluorescens* HP-72-Br5 which do not have an antagonistic property but have a controlling effect upon plant diseases.

Among the above-mentioned novel *Pseudomonas fluorescens*, specific strains have a good antagonistic property against plant pathogenic fungi of the genera Pythium, Rhizoctonia, Sclerotinia and Gaeumannomyces and reveal an especially excellent antagonistic property against *Pythium aphanidermatum, Rhizoctonia solani, Sclerotinia homoecarpa* and *Gaeumannomyces graminis*.

The novel *Pseudomonas fluorescens* of the present invention settles down well in the rhizosphere of a plant, i.e. the surface of roots, the inside of roots and the soil immediately surrounding roots. Accordingly, the *Pseudomonas fluorescens* of the invention is able to reveal its antagonistic property against plant pathogenic fungi extremely well, and yet able to promote the elongation of the root system and leaves of a plant to thereby promote its growth.

The novel *Pseudomonas fluorescens* strain found by the present inventors which exhibits good growth in the rhizosphere of a plant, has a plant growth promoting effect, and produces a PCR product that forms a band at about 800 bp as described above was designated *Pseudomonas fluorescens* HP-72 and deposited at the National Institute of Bioscience and Human-technology, Agency of Industrial Science and Technology under the accession number of FERM BP-5885.

Further, three variants of *Pseudomonas fluorescens* HP-72 were designated *Pseudomonas fluorescens* HP-72-B13, *Pseudomonas fluorescens* HP-72-Br3 and *Pseudomonas fluorescens* HP-72-Br5, respectively. Of these three variants, *Pseudomonas fluorescens* HP-72-B13 and *Pseudomonas fluorescens* HP-72-Br5 were deposited at the National Institute of Bioscience and Human-technology, Agency of Industrial Science and Technology under the accession numbers of FERM BP-5884 and FERM BP-5883, respectively.

Accordingly, the present invention includes *Pseudomonas fluorescens* HP-72 (FERM BP-5885), *Pseudomonas fluorescens* HP-72-B13 (FERM BP-5884), *Pseudomonas fluorescens* HP-72-Br3 and *Pseudomonas fluorescens* HP-72-Br5 (FERM BP-5883).

The present invention further relates to a material for controlling plant (such as lawn grass) pathogenic fungi, a plant growth promoting material and a compost comprising the novel *Pseudomonas fluorescens* described above, in particular *Pseudomonas fluorescens* HP-72, *Pseudomonas fluorescens* HP-72-B13, *Pseudomonas fluorescens* HP-72-Br3 or *Pseudomonas fluorescens* HP-72 -Br5 which has an antagonistic property against pathogenic fungi of the genera Pythium, Rhizoctonia, Sclerotinia and Gaeumannomyces and has a DNA portion that forms a PCR product band at about 800 bp when replicated and amplified by PCR using a primer DNA having the base sequence of 5'-GGCAACTGCACAAGCGCCA shown in SEQ ID NO: 1 and a primer DNA having the base sequence of 5'-GCCAATCACGCCCTCAAGCT shown in SEQ ID NO: 2 and then electrophoresed on agarose gel.

PREFERRED EMBODIMENTS OF THE INVENTION

Hereinbelow, the present invention will be described in detail.

The bacteriological properties of the novel strain of the present invention are shown below.

1) *Pseudomonas fluorescens* HP-72

(a) Morphological properties:

*Pseudomonas fluorescens* HP-72 was cultured in King B medium at 28° C. for 3 days and then air dried to thereby prepare a sample for a scanning electron microscope. The results of the examination of its morphological properties are shown in Table 1 below.

TABLE 1

| Morphological Properties of *Pseudomonas fluorescens* HP-72 |
|---|
| A bacillus Having a polar flagellum |

(b) Cultural properties on various media:

The subject strain grows on King B medium and PDA medium at a temperature range of 4–35° C. This strain grows especially well at around 28° C. and produces a fluorescent pigment. It does not grow at 41° C. It forms colonies having a color tone between yellow and orange and being smooth and glossy on the surface of King B medium.

(c) Utilization of carbon sources:

A test of *Pseudomonas fluorescens* HP-2 for its utilization of carbon sources was performed according to the method of Starnier.

Briefly, *Pseudomonas fluorescens* HP-72 was cultured in King B medium at 25° C. for 3 days. Thereafter, cells were dispersed with a whirling blender and subjected to centrifugation to thereby remove the medium components. Then, an equal volume of sterilized water was added to disperse the cells therein. These operations were repeated three times to thereby remove the medium components completely. Thus, an inoculum was prepared. This inoculum was applied to a plate containing Starnier's basal medium supplemented with one of various carbon sources (pH 6.8) (hereinafter referred to as "basal medium A") and a plate containing Starnier's basal medium not supplemented with any carbon source (pH 6.8) (hereinafter referred to as "basal medium B") and cultured at 28° C. for 14 days. Thereafter, the state of growth of cells (*Pseudomonas fluorescens* HP-72) on basal medium A was compared with the state of growth of cells (*Pseudomonas fluorescens* HP-72) on basal medium B (control) to thereby judge the utilization of each carbon source. The results are shown in Table 2 below.

TABLE 2

| Utilization of Carbon Sources in *Pseudomonas fluorescens* HP-72 | |
|---|---|
| D-Glucose | + |
| Trehalose | + |
| Maltose | − |
| Starch | − |
| Inositol | + |
| Mannitol | + |
| Geraniol | − |
| Agipate | + |
| Valine | + |
| Betaine | + |

+: utilize
−: not utilize (d) Other properties of *Pseudomonas fluorescens* HP-72

The properties of *Pseudomonas fluorescens* HP-72 other than those described above are as shown in Table 3 below.

TABLE 3

Other Properties of *Pseudomonas fluorescens* HP-72

| | |
|---|---|
| Gram staining | negative |
| Denitrifying reaction | negative |
| Gelatin degrading ability | positive |
| Starch degrading ability | negative |
| Poly(3-hydroxybutyric acid) degrading ability | negative |
| Production of fluorescent pigment | positive |
| Inhibition reaction by pyocyanin | negative |
| Oxidase activity | positive |
| Growth at 4° C. | positive |
| Growth at 41° C. | negative |

2) *Pseudomonas fluorescens* HP-72-Br3
   State of growth on various media:
   (i) P-1 medium
   Colonies are circular, cream in color, and transparent. The diameter is about ⅓ compared to that of the colonies of HP-72.
   (ii) King B medium
   Colonies are circular, yellow, mucous in the central part and transparent in the peripheral part.
   P-1 medium and King B medium have the following compositions, respectively.

| Composition of P-1 Medium | |
|---|---|
| $KH_2PO_4$ | 0.1% |
| $MgSO_4 \cdot 7H_2O$ | 0.005% |
| KCl | 0.02% |
| $(NH_4)_2SO_4$ | 0.08% |
| Betaine | 0.2% |
| Agar | 1.5% |
| pH 7.2–7.4 | |

| Composition of King B Medium | |
|---|---|
| Proteose peptone No. 3 (Difco) | 20 g |
| $KH_2PO_4$ | 1.5 g |
| $MgSO_4 \cdot 7H_2O$ | 1.5 g |
| Glycerol | 10.0 g |
| Agar | 15.0 g |
| Distilled water | 1000 ml |
| pH 7.2 | |

The properties of this strain other than the state of growth on media are identical with those of *Pseudomonas fluorescens* HP-72.

3) *Pseudomonas fluorescens* HP-72-Br5
   State of growth on various media:
   (i) P-1 medium
   Colonies are circular but indefinite in the peripheral part, white and opaque.
   (ii) King B medium
   Colonies are circular; they become indefinite when production of mucus is excessive; they have an impression of transparency.
   The properties of this strain other than the state of growth on media are identical with those of *Pseudomonas fluorescens* HP-72.

4) *Pseudomonas fluorescens* HP-72-B13
   State of growth on various media:
   (i) P-1 medium
   Colonies are circular and cream to light yellow in color. The central part is slightly convex and has a darker color.
   (ii) King B medium
   Colonies are circular and orange to brown in color. They have an impression of transparency. The central part is slightly convex and has a darker color.

The properties of this strain other than the state of growth on media are identical with those of *Pseudomonas fluorescens* HP-72.

In addition to the bacteriological properties described above, *Pseudomonas fluorescens* HP-72 of the present invention is greatly different from known *Pseudomonas fluorescens* strains (e.g., *Pseudomonas fluorescens* IAM 12001 and IAM 12022 stored at the IAM) in that it has a DNA which produces a PCR product that appears as a band at about 800 bp when replicated and amplified by PCR using a primer DNA having the base sequence of 5'-GGCAACTGCACAAGCGCCA shown in SEQ ID NO: 1 and a primer DNA having the base sequence of 5'-GCCAATCACGCCCTCAAGCT shown in SEQ ID NO: 2 and then electrophoresed on agarose gel. The above-mentioned known strains do not produce a PCR product that appears as a band at about 800 bp (i.e., they do not have a DNA which produces a PCR product that appears as a band at about 800 bp).

The confirmation of whether a *Pseudomonas fluorescens* strain has such a DNA that produces a PCR product of about 800 bp can be performed as follows.

Method for confirming the presence or absence of a DNA which produces an approx. 800 bp PCR product (1) The primer DNA represented by SEQ ID NO:1 (hereinafter referred to as "primer SP6-1") and the primer DNA represented by SEQ ID NO:2 (hereinafter referred to as "primer SP6-2") are added to a DNA mixture from a *Pseudomonas fluorescens* strain to be tested or a culture thereof and a DNA fragment of interest is selectively replicated and amplified. In this case, the replication and amplification of the DNA mixture from the *Pseudomonas fluorescens* strain with primers SP6-1 and SP6-2 can be performed based on the PCR method which has been widely used for replicating and amplifying a specific DNA using primers. The three reactions of 1) dissociation of the double strand in each DNA molecule in the DNA mixture into single strands, 2) the annealing of primer SP6-1 and primer SP6-2 to a single strand and 3) synthesis of a complementary strand by DNA polymerase are usually repeated for 20–50 times for replication and amplification. As the DNA polymerase used for this purpose, a thermoresistant DNA polymerase which does not lose its activity in the dissociation reaction at about 90–95° C. is preferable.

(2) The DNA mixture which has undergone the replication and amplification treatment described in (1) above is electrophoresed on agarose gel and then stained with ethidium bromide or the like. Then, appearance of a band at about 800 bp is examined. Thus, it can be confirmed whether the *Pseudomonas fluorescens* strain tested has a DNA which produces a PCR product of about 800 bp.

More specifically (but not restrictively), whether a *Pseudomonas fluorescens* strain has a DNA which produces a PCR product of about 800 bp can be examined as follows, for example.

(i) A *Pseudomonas fluorescens* strain to be tested is cultured in a liquid medium (King B medium) at 28° C. for 3 days and then centrifuged at 10000 rpm for 5 minutes to harvest cells. After the cells were washed with sterilized water, the DNA was separated and collected by conventional methods to thereby prepare a solution of DNA mixture.

(ii) To the solution of DNA mixture obtained in (i) above, specific primers SP6-1 and SP6-2 and Ampli Taq DNA Polymerase (product name; Perkin-Elmer Cetus) as a DNA polymerase were added, and a DNA fragment of interest was replicated and amplified by the PCR shown in Table 4 below.

TABLE 4

PCR with Specific Primers SP6-1 and SP6-2

Reaction Solution:

| | |
|---|---|
| 10× Buffer[1] | 5.0 µl |
| 25 mM MgCl$_2$ | 2.0 µl |
| dNTP[2] (2.5 mM each) | 3.0 µl |
| 5 µM Primers[3] | 2.0 µl |
| Solution of DNA mixture from each tube | 50 ng |
| Ampli Taq DNA Polymerase | 1 U |
| Sterilized distilled water to give a total volume of | 50 µl |

Replication/Amplification Apparatus (SNA Thermal Cycler):

Model 1480 (Perkin-Elmer Cetus)

PCR:

| | |
|---|---|
| 1st stage: | heating at 95° C. for 1 minute |
| 2nd stage: | 30 cycles of heating at 94° C. for 30 seconds/at 62° C. for 20 seconds/at 72° C. for 90 seconds |
| 3rd stage: | heating at 72° C. for 5 minutes |

[1] 100 mM Tris-HCl buffer (pH 8.3), 500 mM KCl, 15 mM MgCl$_2$ and 0.01% (w/v) gelatin
[2] Each of dATP, dCTP, dGTP and dTTP is dissolved in distilled water at a concentration of 2.5 mM.
[3] Specific primers SP6-1 and SP6-2 are used in a ratio of 1:1.

(iii) The DNA fragment obtained through replication and amplification by the PCR described in (ii) above is electrophoresed on 1.0% agarose gel using TAE buffer [40 mM Tris acetate/i mM EDTA (pH 8.0)]. Then, the DNA is stained with ethidium bromide for color formation to determine if a band is appearing at about 800 bp.

(iv) If a band is appearing at about 800 bp. as a result of the procedures in (iii) above, it is confirmed that the *Pseudomonas fluorescens* strain tested has a DNA which is specifically replicated and amplified with primer SP6-1 and primer SP6-2. On the other hand, if a band is not appearing at about 800 bp on the agarose gel, it is confirmed that the *Pseudomonas fluorescens* strain tested does not have a DNA which is specifically replicated and amplified with primer SP6-1 and primer SP6-2.

*Pseudomonas fluorescens* HP-72 which is the novel *Pseudomonas fluorescens* strain having a DNA that produces a PCR product appearing as a band at about 800 bp on agarose gel has been isolated from the root of bent grass variety penncross planted at a site of Nisshin Flour Milling Co., Ltd.

*Pseudomonas fluorescens* HP-72-B13, *Pseudomonas fluorescens* HP-72-Br3 and *Pseudomonas fluorescens* HP-72-Br5 have been obtained by mutagenizing *Pseudomonas fluorescens* HP-72 with N-methyl-N-nitro-N-nitrosoguanidine and screening the resultant strains by replica plating method.

The novel *Pseudomonas fluorescens* strain of the present inventions particularly, *Pseudomonas fluorescens* HP-72 and *Pseudomonas fluorescens* HP-72-B13 have a high antagonistic property against plant pathogenic fungi of the genera Pythium, Rhizoctonia, Sclerotinia and Gaeumannomyces, particularly, *Pythium aphanidermatum, Rhizoctonia solani, Sclerotinia homoeocarpa* and *Gaeumannomyces graminis*. On the other hand, *Pseudomonas fluorescens* HP-72-Br3 and *Pseudomonas fluorescens* HP-72-Br5 do not have an antagonistic property against the pathogenic fungi described above (see Table 14, infra). However, any of these strains has an excellent controlling effect on various plant diseases caused by plant pathogenic fungi.

Therefore, a material comprising the novel *Pseudomonas fluorescens* strain described above, particularly, *Pseudomonas fluorescens* HP-72, *Pseudomonas fluorescens* HP-72-B13, *Pseudomonas fluorescens* HP-72-Br3 or *Pseudomonas fluorescens* HP-72-Br5 is effective as a material for controlling plant (e.g., lawn grass) pathogenic fungi. Also, a compost comprising the above strain is effective as a compost which is able to grow plants such as lawn grass and, at the same time, to control the pathogenic fungi described above. The present invention includes such a material for controlling plant pathogenic fungi and such a compost in the scope of the invention.

Further, the novel *Pseudomonas fluorescens* strains of the present invention, particularly, *Pseudomonas fluorescens* HP-72, *Pseudomonas fluorescens* HP-72-B13, *Pseudomonas fluorescens* HP-72-Br3 and *Pseudomonas fluorescens* HP-72-Br5 have an action to promote the elongation of the root system and leaves of plants such as lawn grass. Thus, they are effective for promoting the growth of plants such as lawn grass.

Therefore, a material comprising the novel *Pseudomonas fluorescens* strain described above, particularly, *Pseudomonas fluorescens* HP-72, *Pseudomonas fluorescens* HP-72-B13, *Pseudomonas fluorescens* HP-72-Br3 or *Pseudomonas fluorescens* HP-72-Br5 is effective as a growth promoting material for plants such as lawn grass. Also, a compost comprising the strain has an enhanced effect on the growth of plants such as lawn grass. The present invention includes such a plant growth promoting material and a compost in the scope of the invention.

When the controlling material, growth promoting material or compost of the invention comprising the novel *Pseudomonas fluorescens* strain is applied to a plant such as lawn grass, a controlling material with a high control effect or a growth promoting material or a compost with a high growth promoting effect can be obtained if the *Pseudomonas fluorescens* strain has been cultured and grown in the material or the compost. The culturing of the strain may be performed by conventional methods using a medium conventionally used for the culture of known *Pseudomonas fluorescens* (e.g., King B medium). In this case, the novel *Pseudomonas fluorescens* strain can be grown by inoculating the strain into a sterilized medium and culturing at 25–30° C. for 2–4 days.

After the cultivation, proliferated cells are harvested by an appropriate method such as centrifugation and washed with purified water or the like, if necessary. Thus, cells are obtained. The resultant wet cells may be used as a material for controlling pathogenic fungi of plants such as lawn grass as they are. However, it is preferable to allow such wet cells to be adsorbed on an adsorbent since the cell growth can be maintained at a stable state. As the adsorbent, any adsorbent may be used as long as it can adsorb the microorganism physically or chemically. For example, adsorptive mineral materials such as vermiculite, zeolite (particularly, powder- or granular-type); carbons such as charcoal and active carbon; chemically synthesized porous polymers and the like may be used.

As a method for adsorbing wet cells on an adsorbent, wet cells may be mixed with the adsorbent as they are. Alternatively, wet cells may be dispersed in 1 to 5 volumes of water and then mixed with the adsorbent. The ratio between wet cells and an adsorbent is not particularly limited. Usually, 1 to 3 weight parts of an adsorbent is used per 1 weight part of wet cells.

The thus obtained wet cells adsorbed on an adsorbent (hereinafter referred to as the "wet cell adsorbent") may be applied to lawn grass in that state. Alternatively, this wet cell adsorbent may be semi-dried until the moisture content becomes about 10–30 weight percent and then applied to lawn grass or stored in the semi-dried state. When a semi-drying treatment is performed, it is necessary to perform it at a temperature which does not affect the growth of the cells. Usually, the drying is performed while maintaining the temperature of the wet cell adsorbent at about 25–40° C.

The wet cell adsorbent prepared above or a semi-dried product thereof may be added to a compost or other components and then applied to a plant such as lawn grass, instead of applying them directly. In particular, when the wet cell adsorbent or the semi-dried product is added to a compost for lawn grass, a compost can be obtained which has a high antagonistic property against lawn grass pathogenic fungi of the genera Pythium, Rhizoctonia, Sclerotinia and Gaeumannomyces, particularly, *Pythium aphanidermatum, Rhizoctonia solani, Sclerotinia homoeocarpa* and *Gaeumannomyces graminis* together with a fertilizer effect. A wet cell adsorbent or a semi-dried product thereof can be added to a compost of which the preparation has been completed and used as a mixture.

When the novel *Pseudomonas fluorescens* strain of the present invention is added to a powdery compost with a relatively high moisture content which has not undergone granulation treatment or the like used as a mixture, it is preferred that the moisture content of the compost after the addition of the novel strain be 15 weight percent or less. That will results in a compost in which the *Pseudomonas fluorescens* strain can survive and grow well.

Also, it is preferred that about $10^6$–$10^9$ cells of the novel *Pseudomonas fluorescens* strain be contained per 1 g (converted into dry weight) of the compost immediately after preparation.

Since the novel *Pseudomonas fluorescens* of the invention is killed at 41° C. or above, particularly at 42° C. or above, it is necessary to add the novel *Pseudomonas fluorescens* to a compost when its fermentation has been almost completed and thus its temperature will not rise beyond 40° C. in the preparation of a compost comprising the microorganism.

When the novel *Pseudomonas fluorescens* of the invention is used in the form of a dried, granular organic fertilizer, it is desirable to make the moisture content of the granular organic fertilizer about 7–15 weight percent, preferably 9–11 weight percent. That can allow the novel *Pseudomonas fluorescens* to survive and grow well in the granular organic fertilizer.

As a method for preparing a granular organic fertilizer comprising the novel *Pseudomonas fluorescens* of the invention, it can be prepared, for example, by coating a core substance such as zeolite with an organic material (e.g., organic fertilizer) comprising the novel *Pseudomonas fluorescens*, culturing the microorganism at 10–30° C. for 1–7 days, and drying the resultant material so that its moisture content becomes 5–12 weight percent as described above while keeping the material temperature under 40° C. In this case, it is also preferred that about $10^6$–$10^9$ cells of the novel *Pseudomonas fluorescens* be contained per 1 g of the granular organic fertilizer after drying treatment.

The compost of the present invention is especially effective for lawn grass. When it is applied to lawn grass such as Korean lawn grass, *Zoysia japonica*, bent grass, perennial ryegrass and Bermuda bluegrass, the novel *Pseudomonas fluorescens* contained in the compost grows well in the rhizosphere of lawn grass (i.e. the surface of roots, the inside of roots and the soil immediately surrounding roots) and promotes the growth of lawn grass as an organic fertilizer to thereby promote the elongation of the root system, leaves and the like. At the same time, the novel *Pseudomonas fluorescens* in the compost reveals a high antagonistic property against the above-mentioned lawn grass pathogenic fungi of the genera Pythium, Rhizoctonia, Sclerotinia and Gaeumannomyces, particularly, *Pythium aphanidermatum, Rhizoctonia solani, Sclerotinia homoeocarpa* and *Gaeumannomyces graminis* and controls these pathogenic fungi to thereby allow lawn grass to grow healthy.

When the compost of the invention is applied to lawn grass, usually, the application rate is about 50–500 g per 1 $m^2$ of lawn grass. The compost may be applied to lawn grass by sprinkling or by other methods.

However, the application of the material for controlling plant pathogenic fungi, the plant growth promoting material and the compost of the invention is not limited to lawn grass. They can be used for controlling other plant diseases caused by pathogenic fungi of the genera Pythium, Rhizoctonia, Sclerotinia and Gaeumannomyces. Also, they can be used for the growth promotion of other plants.

Hereinbelow, the present invention will be described in more detail with reference to the following Examples, which should not be construed as limiting the present invention.

EXAMPLE 1

Preparation of a Compost Comprising *Pseudomonas fluorescens* HP-72

(1) *Pseudomonas fluorescens* HP-72 was cultured in King B medium at 28° C. for 3 days.

(2) Six weight parts of a compost was mixed with 100 weight parts of water and sterilized at 121° C. for 15 minutes. To 100 ml of the resultant mixture, 5 ml of the culture solution of *Pseudomonas fluorescens* HP-72 obtained in (1) above was added and placed in a 500 ml Erlenmeyer flask. Total 5 Erlenmeyer flasks were prepared in the same manner. Cells in each flask were cultured at 28° C. for 3 days under shaking. After the cultivation, all of the contents of the 5 Erlenmeyer flasks were added to 30 L of a mixture obtained by mixing 100 weight parts of water and 3 weight parts of the compost and sterilizing at 121° C. for 20 minutes. The resultant mixture was cultured in a 40 L jar fermenter (Tokyo Rikaki) at 28° C. for 3 days.

(3) Separately from the above, a mixture composed of 50 weight parts of wheat bran, 4.8 weight parts of zeolite and 20 weight parts of vermiculite was mixed homogeneously in a large mixer. Then, 35.0 weight parts of water was added thereto and sterilized with superheated steam. The moisture content of the mixture after the sterilization treatment was about 40%. To this mixture, 0.08 weight part each of *Streptomyces flaveolus* (IFO 12768) and *Bacillus circulars* (IFO 13640) were added and mixed homogeneously. Thereafter, slaked lime powder was added thereto to adjust the pH of the mixture at 9.2. This mixture was piled up 20 cm in thickness in a fermentation chamber in which the atmospheric temperature was adjusted at 25° C., and then fermentation was initiated. During fermentation, the pH of the mixture was continuously measured and, when the pH was coming out of the range of 6.5–8.5, slaked lime powder or an aqueous solution of monosodium phosphate was added to keep the pH within the range of 6.5–8.5. Further, the piled mixture was turned upside down almost every other day during fermentation to make the temperature of the mixture uniform. Thus, the mixture was fermented for 15 days under aerobic conditions to prepare a fermented product.

(4) 100 kg of the fermented product obtained in (3) above was placed in a horizontal mixer and sterilized for 30 minutes by agitating while blowing steam thereinto. After leaving for 1 day for cooling, the product was again sterilized for 30 minutes by agitating while blowing steam thereinto. Then, cooling water was circulated in the overcoat of the mixer to lower the product temperature to 28° C. To the resultant product, 30 L of the culture solution obtained in (2) above was added and agitated sufficiently to thereby obtain a compost comprising *Pseudomonas fluorescens* HP-72.

EXAMPLE 2

Preparation of a Material for Controlling Plant Pathogenic Fungi and a Plant Growth Promoting Material Comprising *Pseudomonas fluorescens* HP-72

Ten kilograms of zeolite (Zeolite 2070; Nitto Funkako) was placed in a pan mixer. Then, 5 kg of the compost comprising *Pseudomonas fluorescens* HP-72 prepared in Example 1 was added thereto and the moisture content was adjusted to 36 weight percent by adding water. The resultant mixture was agitated for 10 minutes at a low speed. After the agitation, the mixture was transferred to a plastic container and culture at 28° C. for 3 days. Thereafter, the mixture was dried in a fluidized bed dryer (Takeko Seisakusho) so that the entrance temperature was 100° C., the temperature of the mixture was 41° C. or below, and the moisture content was 12 weight percent or less. Thus, a material containing *Pseudomonas fluorescens* HP-72 at a rate of $3.0 \times 10^8$ CFU/g was prepared which is to be used as a material for controlling plant pathogenic fungi and a plant growth promoting material.

EXAMPLE 3

Investigation into the State of Growth of *Pseudomonas fluorescens* HP-72

(1) A piece about 11 cm in diameter and about 8 cm in depth (hereinafter called the "sod") was hollowed out from a sand green of bent grass variety penncross in which the absence of *Pseudomonas fluorescens* HP-72 had been confirmed in advance.

(2) The material for controlling plant pathogenic fungi (plant growth promoting material) containing *Pseudomonas fluorescens* HP-72 at a rate of $3.0 \times 10^8$ CFU/g prepared in Example 2 and a material for controlling plant pathogenic fungi prepared in a similar manner using known *Pseudomonas fluorescens* (IAM 12022) (the IAM 12022 content: $5.0 \times 10^8$ CFU/g) were applied to the sod obtained in (1) above at a rate of 100 g/m² each. Then, the sod was placed in a gross cabinet and kept for 15 days under the repetition of 12 hours light (30° C.) and 12 hours dark (20° C.). Thereafter, the settling properties in the rhizosphere of the plant in *Pseudomonas fluorescens* HP-72 and the known *Pseudomonas fluorescens* applied to the sod were compared as follows.

(3) Briefly, 2 days, 7 days and 14 days after the application of *Pseudomonas fluorescens* HP-72 to the sod, a portion of the sod 0–15 cm in depth was taken out and separated into a root portion and a soil portion with a small amount of root.

(4) The root portion obtained in (3) above was washed with sterilized water sufficiently (10 times) until the adhering of soil grains was no longer observed with the eyes. Then, the portion was ground in a sterilized mortar to prepare a sample. About 1 g of this sample was cultured at 28° C. for 3 days according to the plate count method using P-1 medium which selectively propagates those bacteria belonging to fluorescent pseudomonas (*Pseudomonas fluorescens, Pseudomonas putida, Pseudomonas aeruginosa*). Then, the number of resultant colonies of fluorescent pseudomonas was counted to obtain the bacterial count of the fluorescent pseudomonas growing in the root of bent grass variety penncross (Br).

(5) From each of the colonies of fluorescent pseudomonas obtained by the cultivation in (4) above, DNA was obtained by conventional methods and added to a reaction solution (of which the composition is shown in Table 4) so that the amount of DNA was 50 ng. To this solution, primer SP6-1, primer SP6-2 and Ampli Taq DNA Polymerase (product name; Perkin-Elmer Cetus) as a DNA polymerase were added. Then, DNA fragments were replicated and amplified by PCR as shown in Table 4.

(6) Ten microliters of the reaction solution obtained by PCR in (5) above was electrophoresed on 1.0% agarose gel using Mupid-2 (Cosmo Bio) and stained with ethidium bromide for color formation. The appearance of a band at about 800 bp was examined. Then, the number of colonies of the *Pseudomonas fluorescens* having a DNA that forms a PCR band at about 800 bp (i.e., *Pseudomonas fluorescens* HP-72) was counted (Cr). According to Formula 1 below, the ratio of the bacterial count of *Pseudomonas fluorescens* HP-72 to the bacterial count of the fluorescent pseudomonas growing in the root of bent grass variety penncross (Ar) (%) was calculated.

(7) The series of steps described above were performed 3 times to determine the bacterial count of the fluorescent pseudomonas (Br) and the bacterial count of the *Pseudomonas fluorescens* HP-72 (Cr) growing in the root of bent grass variety penncross and calculate the ratio of the latter (Ar) (%). The average values from the 3 times of determination/calculation are shown in Table 5 below.

$$Ar(\%) = (Cr/Br) \times 100 \quad \text{(Formula 1)}$$

where

Ar: the ratio of the bacterial count of the *Pseudomonas fluorescens* HP-72 to the bacterial count of the fluorescent pseudomonas growing in the root of bent grass variety penncross;

Br: the bacterial count of the fluorescent pseudomonas growing in the root of bent grass variety penncross; and Cr: the bacterial count of the *Pseudomonas fluorescens* HP-72 growing in the root of bent grass variety penncross.

(8) On the other hand, the soil portion obtained in (3) above was ground in a commercial coffee mill which had been sterilized at 50° C. for 1 hour (sterilization of pseudomonas bacteria) to thereby prepare a sample. This sample (1.0 g) was cultured in the same manner as the root portion was cultured above using P-1 medium which selectively propagates those bacteria belonging to fluorescent pseudomonas. The number of resultant colonies of fluorescent pseudomonas was counted to obtain the bacterial count of the fluorescent pseudomonas growing in the soil portion of bent grass variety penncross (Bs).

(9) From each of the colonies obtained by the cultivation in (8) above, DNA was obtained by conventional methods. Then, as described in (5) and (6) above, DNA fragments were replicated and amplified by PCR and electrophoresed to examine the appearance of a band at about 800 bp.

(10) The number of colonies of *Pseudomonas fluorescens* HP-72 having a DNA that forms a PCR band at about 800 bp was counted (Cs). According to Formula 2 below, the ratio of the number of the *Pseudomonas fluorescens* HP-72 cells to the number of the fluorescent pseudomonas cells growing in the soil portion of bent grass variety penncross (As) (%) was calculated.

(11) The series of steps described above were performed 3 times to determine the bacterial count of the fluorescent pseudomonas (Bs) and the bacterial count of the *Pseudomonas fluorescens* HP-72 (Cs) growing in the soil portion of bent grass variety penncross and calculate the ratio of the latter (As) (%). The mean values from the 3 times of determination/calculation are shown in Table 5 below.

$$As(\%)=(Cs/Bs)\times 100 \quad \text{(Formula 2)}$$

where

As: the ratio of the bacterial count of the *Pseudomonas fluorescens* HP-72 to the bacterial count of the fluorescent pseudomonas growing in the soil portion of bent grass variety penncross;

Bs: the bacterial count of the fluorescent pseudomonas growing in the soil portion of bent grass variety penncross; and Cs: the bacterial count of the *Pseudomonas fluorescens* HP-72 growing in the soil portion of bent grass variety penncross.

TABLE 5

| | Bacterial count of HP-72[1)] (CFU/g) | | Ratio of HP-72[1)] (%) | |
|---|---|---|---|---|
| | Soil (Cs) | Root (Cr) | Soil (As) | Root (Ar) |
| Immediately before the application | 0 | 0 | 0 | 0 |
| 2 days after the application | $4.4 \times 10^6$ | $1.5 \times 10^5$ | 65 | 50 |
| 7 days after the application | $2.8 \times 10^5$ | $3.3 \times 10^5$ | 29 | 79 |
| 14 days after the application | $2.7 \times 10^5$ | $1.5 \times 10^5$ | 41 | 89 |

[1)]*Pseudomonas fluorescens* HP-72

From the results shown in Table 5 above, it is seen that the ratio of *Pseudomonas fluorescens* HP-72 growing in the root portion (e.g., rhizosphere) of lawn grass becomes higher than that in the soil portion as its growth proceeds. Thus, *Pseudomonas fluorescens* HP-72 is able to control pathogenic fungi directly in the root of lawn grass and to protect lawn grass from pathogenic fungi more effectively.

EXAMPLE 4

(1) In this Example, the material for controlling plant pathogenic fungi comprising *Pseudomonas fluorescens* HP-72 prepared in Example 2 was applied at a rate of 150 g/m² on Oct. 11, 1994 to a field experiment plot (100 m²) of bent grass variety penncross sand green in a golf course (H Country Club, Tochigi Pref.). The absence of *Pseudomonas fluorescens* HP-72 in the experiment plot was confirmed in advance (detection limit $<10^3$ cells). Then, a field experiment was performed over 93 days.

(2) In the field experiment mentioned in (1) above, a sod was hollowed out from the sand green of the experiment plot in the same manner as in Example 3 at 61 days and 93 days after the application of the material for controlling plant pathogenic fungi comprising *Pseudomonas fluorescens* HP-72, and the determination of bacterial counts were performed in the same manner as in Example 3. Briefly, the bacterial count of the fluorescent pseudomonas (Br) and the bacterial count of the *Pseudomonas fluorescens* HP-72 (Cr) growing in the root of bent grass variety penncross were determined and, from these values, the ratio of the latter (Ar) (%) was calculated. Further, the bacterial count of the fluorescent pseudomonas (Bs) and the bacterial count of the *Pseudomonas fluorescens* HP-72 (Cs) growing in the soil portion of bent grass variety penncross were determined and, from these values, the ratio of the latter (As) (%) was calculated. The results are shown in Table 6 below.

TABLE 6

| | Bacterial count of HP-72[1)] (CFU/g) | | Ratio of HP-72[1)] (%) | |
|---|---|---|---|---|
| | Soil (Cs) | Root (Cr) | Soil (As) | Root (Ar) |
| Immediately before the application | 0 | 0 | 0 | 0 |
| 61 days after the application | $2.2 \times 10^5$ | $1.3 \times 10^5$ | 32 | 91 |
| 93 days after the application | $2.4 \times 10^5$ | $3.2 \times 10^5$ | 36 | 88 |

[1)]*Pseudamonas fluorescens* HP-72

From the results shown in Table 6 above, it is seen that the ratio of *Pseudomonas fluorescens* HP-72 growing in the root portion (e.g., rhizosphere) of lawn grass also becomes higher than that in the soil portion as its growth proceeds when applied in the filed. Thus, *Pseudomonas fluorescens* HP-72 is able to control pathogenic fungi directly in the root and to protect lawn grass from pathogenic fungi more effectively.

A control field experiment was performed at the same time in the same place (where the absence of *Pseudomonas fluorescens* HP-72 had been confirmed in advance) over 95 days in the same manner as in Example 4 except that a material for lawn grass not containing *Pseudomonas fluorescens* HP-72 prepared as described in Example 2 was used. During the period of this experiment, it was confirmed that *Pseudomonas fluorescens* HP-72 was not present in the soil portion nor in the root (detection limit $<10^3$ cells).

EXAMPLE 5

Test of Antagonistic Property against Lawn Grass Pathogenic Fungi by Dual Culture (1) PDA medium (potato dextrose agar medium) was sterilized at 121° C. for 20 minutes in advance. The medium was placed in a sterilized laboratory dish and allowed to become solid. Then, one platinum loopful of *Pseudomonas fluorescens* HP-72 was smeared on the medium as a spot 1 cm inside from the margin. Total 4 laboratory dishes were prepared in the same manner.

(2) Separately from the above, (i) *Sclerotinia homoeocarpa*, the pathogenic fungus causing dollar spot, (ii) *Rhizoctonia solani*, the pathogenic fungus causing brown patch, (iii) *Gaeumannomyces graminis*, the pathogenic fungus causing take-all patch and (iv) *Pythium aphanidermatum*, the pathogenic fungus causing pythium red blight were cultured on PDA medium. Each plate was punched with a sterilized cork borer and the thus prepared sample was inoculated to the laboratory dish prepared in (1) above (on which *Pseudomonas fluorescens* HP-72 had been smeared) at a symmetrical position to that of *Pseudomonas fluorescens* HP-72. The laboratory dish inoculated with (iii) *Gaeumannomyces graminis* was dual cultured at 25° C. and the other dishes were dual cultured at 28° C. for 1 week. Then, the antagonistic property of *Pseudomonas fluorescens* HP-72 against the pathogenic fungi (i) to (iv) was evaluated according to the evaluation standards shown in Table 7 below. The results are shown Table 8 below.

TABLE 7

Standards for Evaluating the Antagonistic Property of
*Pseudomonas fluorescens* HP-72 against Pathogenic Fungi

| | |
|---|---|
| ⊚: | The area of inhibition zone ≧ 7.5 cm$^2$; having a high antagonistic property |
| ○: | 5 cm$^2$ ≦ The area of inhibition zone < 7.5 cm$^2$; having an antagonistic property |
| Δ: | 2.5 cm$^2$ ≦ The area of inhibition zone < 5 cm$^2$; having a slight antagonistic property |
| X: | The area of inhibition zone < 2.5 cm$^2$; having little antagonistic property |

Method for Measuring the Area of Inhibition Zone

On a transparent sheet, 5×5 mm squares were drawn. This sheet was covered on the laboratory dish and the number of squares coming inside of the inhibition zone was counted to obtain the area (1 square=0.25 cm$^2$).

TABLE 8

Test Results on the Antagonistic Property of
*Pseudomonas fluorescens* HP-72 against Pathogenic Fungi

| | Pathogenic fungus | Antagonistic property |
|---|---|---|
| (i) | *Sclerotinia homeocarpa* | ⊚ |
| (ii) | *Rhizoctonia solani* | ⊚ |
| (iii) | *Gaeumannomyces graminis* | ⊚ |
| (iv) | *Pythium aphanidermatum* | ○ |

From the results shown in Table 8, it is seen that *Pseudomonas fluorescens* HP-72 has a good antagonistic property against any of the lawn grass pathogenic fungi of *Sclerotinia homoeocarpa, Rhizoctonia solani, Gaeumannomyces graminis* and *Pythium aphanidermatum* and has a control effect against these pathogenic fungi.

EXAMPLE 6

Investigation into the State of Growth of the Root System of Lawn Grass (1) Ten pots 22×14×6 cm (length×width×depth) having 10 holes 2 mm in diameter at the bottom were prepared. Each pot was filled with a bed soil (composed of 85 weight parts of river sand passing through 2 mm opening, 10 weight part of zeolite and 5 weight parts of vermiculite) so that the soil depth was 4.8 cm. Seeds of bent grass variety penncross (Taki Shubyo) were sown on it at a rate of 10 g/m$^2$ and the same soil used as the bed soil was sprinkled over them 1 mm in thickness. Five pots were used for test plot and the other 5 pots for control plot.

(2) To the 5 pots for test plot prepared in (1), the plant growth promoting material prepared in Example 2 was applied at a rate of 100 g/m$^2$. Then, the seeds were grown under the repetition of 12 hours dark (15° C.) and 12 hours light (22° C.) for 25 days. During this period, grass was trimmed so that the leaf length would not exceed 20 mm. Also, watering was performed once in every three days until water dripped out from the holes provided at the bottom of the pot.

(3) Separately from (2) above, a material in which *Pseudomonas fluorescens* HP-72 had been killed was prepared by adjusting the moisture content of the plant growth promoting material comprising *Pseudomonas fluorescens* HP-72 prepared in Example 2 to 60%, keeping it at 50° C. for 3 hours, and then readjusting its moisture content to 12% or less. This material was applied to the 5 pots for control plot at a rate of 100 g/m$^2$. Then, the seeds were grown under the repetition of 12 hours dark (15° C.) and 12 hours light (22° C.) for 25 days. During this period, grass was trimmed so that the leaf length would not exceed 20 mm. Also, watering was performed once in every three days until water dripped out from the holes provided at the bottom of the pot.

(4) The same growth test consisting of the steps (1)–(3) above was repeated twice further (i.e., total 3 tests were performed for test plot and control plot, respectively).

(5) At the completion of the growth test described in (1)–(4) above, 5 samples of grown up bent grass variety penncross were collected from each pot using a cork borer (20 mm in diameter) so that each sample was 5 cm in depth and contained leaves, roots and soil without fail. These samples were washed with tap water and then washed with sterilized water 10 times. Then, it was confirmed with the eyes that no bed soil was adhering to the root.

(6) For each stock of the bent grass variety penncross washed in (5) above, the length of the longest root was measured and the mean value from the total stocks was calculated. The results are shown in Table 9 below. In the measurement of the root length of bent grass variety penncross, 5 stocks were measured for each sample taken with a cork borer (375 stocks each were measured for test plot and control plot).

(7) The bacterial count of the *Pseudomonas fluorescens* HP-72 growing in the root of the bent grass variety penncross washed in (5) above was obtained in the same manner as described in (4) to (6) in Example 3. The results are shown in Table 9 below. In the determination of the bacterial count of the *Pseudomonas fluorescens* HP-72, one sample from each pot was used (15 samples each were used for test plot and control plot).

TABLE 9

| | Root length (mm) | Bacterial count of HP-72[1] (CFU/g) |
|---|---|---|
| Test plot | 17.5[2] | 2.4 × 10$^6$ |
| Control plot | 7.0[2] | not detected |

[1] *Pseudomonas fluorescens* HP-72
[2] There is a significant difference at a hazard rate of 1%.

From the results shown in Table 9, it is seen that in the test plot where the plant growth promoting material comprising *Pseudomonas fluorescens* HP-72 has been applied, this bacterium grows well in the root of lawn grass and greatly promotes the growth of the root system of lawn grass compared to the control plot where a material not containing this bacterium has been applied.

EXAMPLE 7

Investigation into the State of Growth of the Leaves of Lawn Grass (1) Eighteen sods about 10 cm in diameter of bent grass variety penncross were taken from a nursery of a golf club (Sano City, Tochigi Pref.). Nine sods were used for test plot and the other 9 sods for control plot.

(2) To each of the sods taken in (1) above, a liquid fertilizer (Fukugo 12–5–7 manufactured by ZENNO) was applied so that 1 g of nitrogen was applied to each sod. Then, the bent grass was grown in a certified incubator under the conditions of 12 hours light (22° C.) and 12 hours dark (15° C.) for 1 week.

(3) To the test plot (9 sods) grown in (2) above, the plant growth promoting material comprising *Pseudomonas fluorescens* HP-72 prepared in Example 2 was applied at a rate of 100 g/m². Then, the sods were grown under the repetition of 12 hours dark (15° C.) and 12 hours light (22° C.) for 25 days while providing watering once in every three days until water dripped out from the holes. During this period, grass was trimmed so that the height of the trimmed grass became 10 mm once in every three days.

(4) After the 1 week growth period described in (3) above, the bacterial count of the *Pseudomonas fluorescens* HP-72 growing at the root portion of bent grass variety penncross was determined in the same manner as in Example 6. Thereafter, the cultivation of bent grass was continued while providing watering once in every three days until water dripped out from the holes. During the cultivation, bent grass was trimmed once in every three days (total 6 times) so that the height of the trimmed grass became 10 mm. The total amount of grass trimmed each time was measured and the mean value per sod was calculated. The results are shown in Table 10.

(5) A material in which *Pseudomonas fluorescens* HP-72 had been killed was prepared by adjusting the moisture content of the plant growth promoting material comprising *Pseudomonas fluorescens* HP-2 prepared in Example 2 to 60%, keeping it at 50° C. for 3 hours, and then readjusting its moisture content to 12% or less. This material was applied to the control plot (9 sods) grown in (2) above at a rate of 100 g/m². Then, the sods were grown under the conditions of 12 hours light (22° C.) and 12 hours dark (15° C.) for 1 week while providing watering once in every three days until water dripped out from the holes provided at the bottom of the pot. During this period, grass was trimmed once in every three days so that the height of the trimmed grass became 10 mm.

(6) After the 1 week growth period described in (5) above, the bacterial count of the *Pseudomonas fluorescens* HP-72 growing at the root portion of bent grass variety penncross was determined in the same manner as in Example 6. Thereafter, trimming was performed 6 times and the total amount of grass trimmed each time was measured as described in (4) above. The results are shown in Table 10 below.

From the amount of grass trimmed in the test plot and the amount of grass trimmed in the control plot, the ratio of increase in the amount of trimming was calculated by the following formula. The results are shown in Table 10 below.

The ratio of increase in the amount of trimming (%)=

$$[(A-B)/B] \times 100$$

where A=the amount of grass trimmed in the test plot (g)
B=the amount of grass trimmed in the control plot (g)

TABLE 10

| | Amount of grass trimmed per sod (g) | | | | | | HP-72[1] count |
|---|---|---|---|---|---|---|---|
| | 1st | 2nd | 3rd | 4th | 5th | 6th | (CFU/g) |
| Test Plot | 0.44 | 0.55 | 0.47 | 0.83 | 0.53 | 0.77 | $2.4 \times 10^6$ |
| Control Plot | 0.35 | 0.45 | 0.40 | 0.75 | 0.41 | 0.63 | not detected |
| Ratio of Increase[2] | 25.7 | 25.0 | 17.5 | 10.7 | 29.3 | 22.2 | — |

[1]The bacterial count of the *Pseudomonas fluorescens* HP-72 growing in the root system one week after the application of the material of Example 2 comprising this bacterium or the material not containing this bacterium.
[2]The ratio of increase in the amount of trimming (%) (the average ratio of increase in the amount of trimming from the 1st to 6th trimming = 21.7%)
Note: There is a significant difference at a hazard rate of 5% in the amount of grass trimmed at the 1st, 2nd, 4th, 5th and 6th trimming.

From the results shown in Table 10 above, it is seen that in the test plot where the plant growth promoting material comprising *Pseudomonas fluorescens* HP-72 has been applied, this bacterium grows well in the root system of lawn grass and that the amount of grass trimmed each time is greater compared to the control plot where a material not containing this bacterium has been applied. Thus, it is seen the growth of leaves of lawn grass is promoted by this bacterium.

EXAMPLE 8

Control Test on the Plant Pathogenic Fungus *Rhizoctonia solani*

(1) Twenty-seven sods about 10 cm in diameter of bent grass variety penncross were taken from a nursery of a golf club (Sano City, Tochigi Pref.). To each sod, a liquid fertilizer (Fukugo 12-5-7 manufactured by ZENNO) was applied so that 1 g of nitrogen was applied per 1 sod. Then, the sods were grown in a certified incubator under the conditions of 12 hours light (22° C.) and 12 hours dark (15° C.) for 1 week. Thus, 9 sods for test plot, 9 sods for control plot I and 9 sods for control plot II were obtained.

(2) To the 9 sods for test plot grown in (1) above, the plant growth promoting material comprising *Pseudomonas fluorescens* HP-72 prepared in Example 2 was applied at a rate of 100 g/m². To the 9 sods for control plot I, a material in which *Pseudomonas fluorescens* HP-72 had been killed was applied at a rate of 100 g/m². This material was prepared by adjusting the moisture content of the plant growth promoting material of Example 2 comprising *Pseudomonas fluorescens* HP-2 to 60%, keeping it at 50° C. for 3 hours, and then readjusting its moisture content to 12% or less. To the 9 sods for control plot II, the material in which *Pseudomonas fluorescens* HP-72 had been killed was applied in the same manner as in control plot I, and subsequently a 500-fold diluent of an agricultural chemical (Grass-Ten Wettable Powder; containing isoprothiolan 20% and flutolanil 25%; Japan Agricultural Chemicals Co., Ltd.) was applied at a rate of 1 L/m² [applied 1 day before the inoculation of the pathogenic fungus described in (3) below].

(3) The sods for test plot, control plot I and control plot II treated in (2) above were grown under the conditions 12 hours light (22° C.) and 12 hours dark (15° C.) for 1 week while providing watering once in every three days until water dripped out from the holes provided at the bottom of the pot. During this period, trimming was performed once in every three days so that the height of the trimmed grass became 10 mm.

(4) After the 1 week growth period described in (3) above, a hole 1.5 cm in diameter and 3 cm in depth was made in the center of each sod. Into this hole, 2 pieces of a bran pellet containing *Rhizoctonia solani* which causes bent grass leaf blight [obtained by inoculating *Rhizoctonia solani* grown on PDA medium (Difco) into a bran pellet (3.5 mm in diameter, 5 mm in length, moisture content 50%, sterilized at 121° C. for 20 minutes) and culturing at 28° C. for 7 days] were placed. The hole was filled by sprinkling a cover sand (composed of 85 weight parts of river sand passing through 2 mm opening, 10 weight part of zeolite and 5 weight parts of vermiculite).

(5) Subsequently, watering was provided until water dripped from the bottom and the sods were grown at a relative humidity of 100%, at an atmospheric temperature of 25° C., under 12 hours light and 12 hours dark. Seven days, 10 days and 20 days after the inoculation of the pathogenic fungus, 3 panelists observed the sods and determined the disease index for each sod based on the disease indices as shown in Table 11 below. Then, the degree of disease development was calculated by Formula 2 described below. The results are shown in Table 12 below. Also, percent control was determined by Formula 3 described below based on the degree of disease development in control plot I. The results are shown in Table 12 below.

TABLE 11

| Disease Index | Contents |
| --- | --- |
| 4 | 50% or more is infected and withered |
| 3 | The infected and withered portion is ≧10% and <50%. |
| 2 | The infected and withered portion is <10%. |
| 1 | Some leaves are infected and changed to yellow. |
| 0 | Healthy in appearance. |

The Degree of Disease Development=

[Σ(Number of Diseased Sods by Index×Disease Index)]/(Number of Sods Tested×4)      (Formula 2)

Percent Control (%)=

[1−(Degree of Disease in Each Plot/Degree of Disease in Control Plot I]×100      (Formula 3)

(6) Ten days after the inoculation of the pathogenic fungus, samples were taken from each sod 2 cm inside from the margin of the sod with a cork borer 2.0 cm in diameter. From these samples, the stem portions of 20 stocks were collected and washed with tap water until no sand granules were observed with the eyes. Then, these portions were dipped in 70% ethanol to sterilize the surface for 2 minutes. Thereafter, the ethanol was removed by washing with tap water and then the portions were dipped in distilled water for 5 minutes for further washing. These stem portions were inoculated into an aqueous agar medium (agar concentration: 1.5%) supplemented with 300 ppm streptomycin and cultured. Two or three days after the inoculation, cells of filamentous fungi grown up were inoculated into PDA medium and cultured at 28° C. for 3 days. Then, the all of the filamentous fungi and *Rhizoctonia solani* (RS) were confirmed with the eyes and a microscope, and the number of total filamentous fungi and that of RS were determined from the number of colonies on the plate at a specific dilution stage. According to Formula 4 below, the isolation ratio of *Rhizoctonia solani* from the total filamentous fungi appearing on the aqueous agar medium containing streptomycin (RS isolation ratio) was obtained. The results are shown in Table 12 below.

RS Isolation Ratio (%)=

(Number of RS in each plot/Number of total filamentous fungi in each plot)×100      (Formula 4)

TABLE 12

| Degree of Disease | Test Plot (Plot of the Invention) | Control Plot I (No treatment) | Control Plot II (Treated with Ag. Chemical) |
| --- | --- | --- | --- |
| Development | | | |
| After 7 days | 24.4 | 54.2 | 13.9 |
| After 10 days | 27.8ª | 73.1 | 19.4ª |
| After 20 days | 33.3ᵇ | 86.1 | 30.6ᵇ |
| Percent Control | | | |
| After 7 days | 55.0 | — | 74.4 |
| After 10 days | 61.5 | — | 61.5 |
| After 20 days | 61.3 | — | 64.5 |
| RS Isolation Ratio (%) | 0.8 | 29.7 | 0 |

Note: The same small letters indicate that there is not 5% significant difference according to Duncan's multiple range test between them.

From the results shown in Table 12 above, it is seen that the material of the invention for controlling plant pathogenic fungi comprising *Pseudomonas fluorescens* HP-72 is extremely effective for controlling the lawn grass pathogenic fungus *Rhizoctonia solani*.

EXAMPLE 9

(1) In this Example, whether *Pseudomonas fluorescens* HP-72 grows well in the root system of plants other than lawn grass (i.e. wheat, barley tomato and egg plant) or not was tested by a method based on Example 3.

(2) Four pots (10 cm in diameter, 15 cm in depth) having 5 holes about 2 mm in diameter at the bottom were prepared. Each pot was filled with a red soil (bacterial count of fluorescent pseudomonas=$3.4 \times 10^6$ CFU/g; *Pseudomonas fluorescens* HP-72 not detected; pH 6.8) to a depth of 12 cm.

(3) To each pot filled with the red soil in (2) above, the material for controlling plant pathogenic fungi (plant growth promoting material) containing *Pseudomonas fluorescens* HP-72 at a rate of $3.0 \times 10^8$ CFU/g prepared in Example 2 and a material for controlling plant pathogenic fungi prepared as described in Example 2 using a known *Pseudomonas fluorescens* (IAM 12022) (the IAM 12022 content: $5.0 \times 10^8$ CFU/g) were applied at a rate of 100 g/m², respectively. Then, seeds of wheat (variety: Chinese Spring), barley (variety: Sumiremochi), Tomato (variety: Red Cherry) and egg plant (variety: Kokuyo) were sown separately at a ratio of 5 seeds/pot.

(4) Subsequently, the seeds were covered with the red soil described above 5–10 mm in thickness. Watering was performed until water dripped out from the holes at the bottom of the pot. Such watering was performed once in every 7 days. During this period, the plants were grown under the conditions of 12 hours light (at 22° C.) and 12 hours dark (15° C.). Thirty-five days after the sowing, the determination of the bacterial count was conducted only on the root in the same manner as in Example 3. Thus, the bacterial count of the *Pseudomonas fluorescens* HP-72 growing in the root and the ratio of this count to the bacterial count of the fluorescent pseudomonas growing in the root were obtained. The results are shown in Table 13.

TABLE 13

|  | Bacterial count of HP-72[1] (CFU/g) | Ratio of HP-72[1] (%) |
|---|---|---|
| Wheat | $3.5 \times 10^5$ | 58 |
| Barley | $2.8 \times 10^5$ | 48 |
| Tomato | $6.8 \times 10^5$ | 66 |
| Egg plant | $7.6 \times 10^5$ | 74 |

[1]*Pseudomonas fluorescens* HP-72

From the results shown in Table 13, it is seen that *Pseudomonas fluorescens* HP-72 also grows well in the root system, etc. of plants such as wheat, barley, tomato and egg plant.

EXAMPLE 10

*Pseudomonas fluorescens* HP-72-Br3 and *Pseudomonas fluorescens* HP-72-Br5 were compared to their parent strain *Pseudomonas fluorescens* HP-72 on their antagonistic property, plant growth promotion (PGPR) effect and settlement in the root, as well as the degree of disease development and percent control when they are applied.

This experiment was performed under the same conditions as in Example 8. The results are shown in Table 14 below.

In this experiment, bent grass was treated with each of the strains as follows.
No inoculation plot: Bent grass was not treated with *Pseudomonas fluorescens* nor any agricultural chemical. Only the pathogenic Rhizoctonia was inoculated.
HP-72 plot: Bent grass was treated with HP-72 and then the pathogenic Rhizoctonia was inoculated.
HP-72-Br3 plot: Bent grass was treated with HP-72-Br3 and then the pathogenic Rhizoctonia was inoculated.
HP-72-Br5 plot: Bent grass was treated with HP-72-Br5 and then the pathogenic Rhizoctonia was inoculated.
Ag. chem. plot: The pathogenic Rhizoctonia was inoculated the day after the agricultural chemical treatment.
HP-72 plot without inoculation of pathogenic fungus: Bent grass was treated with HP-72 and pathogenic Rhizoctonia was not inoculated.

Effect of the Invention

The material of the invention for controlling plant pathogenic fungi and the compost of the invention both prepared by using a novel *Pseudomonas fluorescens*, particularly, *Pseudomonas fluorescens* HP-72 which has an antagonistic property against pathogenic fungi of the genera Pythium, Rhizoctonia, Sclerotinia and Gaeumannomyces and which has a DNA portion that forms a PCR product band at about 800 bp when replicated and amplified by PCR using a primer DNA having the base sequence of 5'-GGCAACTGCACAAGCGCCA shown in SEQ ID NO: 1 and a primer DNA having the base sequence of 5'-GCCAATCACGCCCTCAAGCT shown in SEQ ID NO: 2 and then electrophoresed on agarose gel can be used effectively for controlling various diseases of plants.

Further, *Pseudomonas fluorescens* HP-72-B13, *Pseudomonas fluorescens* HP-72-Br3 and *Pseudomonas fluorescens* HP-72-Br5 which are variants of *Pseudomonas fluorescens* HP-72 can be used for controlling various diseases of plants when contained in the material for controlling plant pathogenic fungi or the compost of the invention, regardless of the antagonistic properties against pathogenic fungi of the generagenera Pythium, Rhizoctonia, Sclerotinia and Gaeumannomyces.

Since the novel *Pseudomonas fluorescens* of the invention grows better in the rhizosphere of a plant such as the surface of roots than in soil, this microorganism can protect plants from pathogenic fungi directly and extremely effectively.

Furthermore, the plant growth promoting material and the compost of the invention both prepared by using the above-mentioned novel *Pseudomonas fluorescens*, particularly, *Pseudomonas fluorescens* HP-72, *Pseudomonas fluorescens* HP-72-B13, *Pseudomonas fluorescens* HP-72-Br3 or *Pseudomonas fluorescens* HP-72-Br5 promotes the elongation of the root system of a plant such as lawn grass, in particular, the elongation of the root system at the early stage of growth, and also promotes the elongation of leaves. Thus, they are effective for the growth promotion of plants.

According to the present invention, control of plant pathogenic fungi and promotion of plant growth can be achieved without using drugs such as agricultural chemicals and compound fertilizers or with reduced use of them. Therefore, damage to humans and other organisms, pollution of rivers, underground water and soil and destruction of ecosystems and nature resulted from the use of such drugs, poor growth or withering of plants due to inappropriate concentration of fertilizers, infertilization of soil due to repeated application of fertilizers, and the like can be prevented.

TABLE 14

| Strain Used | Antagonistic Property | PGPR Effect[1] (14 days after sowing) | Settlement in Root[2] | Degree of Disease Development | Percent Control |
|---|---|---|---|---|---|
| No inoculation |  | 10.5 |  | 52.5 |  |
| Parent strain HP-72 | + | 18.6 | $3.6 \times 10^6$ | 15.4 | 70.7 |
| Variant HP-72-Br3 | − | 17.3 | $2.9 \times 10^6$ | 12.4 | 76.4 |
| Variant HP-72-Br5 | − | 14.5 | $5.3 \times 10^6$ | 9.6 | 81.7 |
| Agri. chemical plot |  |  | N.D. | 10.2 | 80.6 |
| HP-72 without inoculation of pathogenic fungus |  |  | $4.5 \times 10^6$ | 0.0 |  |

[1]PGPR Effect: The root length of lawn grass 14 days after the sowing was measured. Mean root length from 100 stocks each were compared.
[2]Settlement in Root: The bacterial counts of the HP-72, HP-72-Br3 and HP-72-Br5 adhering on the surface of roots were determined.
N.D. means "not detected".

We claim:

1. An isolated *Pseudomonas fluorescens* having an antagonistic property against plant pathogenic fungi and having a DNA that forms a polymerase chain reaction (PCR) product band at about 800 bp when replicated and amplified by PCR using a primer DNA having the base sequence of 5'-GGCAACTGCACAAGCGCCA shown in SEQ ID NO: 1 and a primer DNA having the base sequence of 5'-GCCAATCACGCCCTCAAGCT shown in SEQ ID NO: 2 and then electrophoresed on agarose gel.

2. The *Pseudomonas fluorescens* of claim 1, which has an antagonistic property against plant pathogenic fungi of the genera Pythium, Rhizoctonia, Sclerotinia and Gaeumannomyces.

3. The *Pseudomonas fluorescens* of claim 1, which has an antagonistic property against the plant pathogenic fungi *Pythium aphanidermatum, Rhizoctonia solani, Sclerotinia homoeocarpa* and *Gaeumannomyces graminis*.

4. The *Pseudomonas fluorescens* of claim 1, which has a property of settling well in the rhizosphere of a plant in soil.

5. The *Pseudomonas fluorescens* of claim 1, which has a plant growth promoting action.

6. Isolated *Pseudomonas fluorescens* HP-72 (FERM BP-5885), isolated *Pseudomonas fluorescens* HP-72-BR13 (FERM BP-5884), or isolated *Pseudomonas fluorescens* HP-72-Br5 (FERM BP-5883).

7. A material for controlling plant pathogenic fungi comprising the *Pseudomonas fluorescens* of claim 1.

8. A plant growth promoting material comprising the *Pseudomonas fluorescens* of claim 1.

9. A compost comprising the *Pseudomonas fluorescens* of claim 1.

10. A material for controlling plant pathogenic fungi comprising one or more microorganisms selected from the group consisting of *Pseudomonas fluorescens* HP-72, *Pseudomonas fluorescens* HP-72-BR13, and *Pseudomonas fluorescens* HP-72-Br5.

11. A plant growth promoting material comprising one or more microorganisms selected from the group consisting of *Pseudomonas fluorescens* HP-72, *Pseudomonas fluorescens* HP-72-BR13, and *Pseudomonas fluorescens* HP-72-Br5.

12. A compost comprising one or more microorganisms selected from the group consisting of *Pseudomonas fluorescens* HP-72, *Pseudomonas fluorescens* HP-72-BR13, and *Pseudomonas fluorescens* HP-72-Br5.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: synthetic pri-DNA (xi) SEQUENCE DESCRIPTION: SEQ ID NO:1:

GGCAACTGCA CAAGCGCCA                    19

(2) INFORMATION FOR SEQ ID NO:2:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: synthetic pri-DNA (xi) SEQUENCE DESCRIPTION: SEQ ID NO:2:

GCCAATCACG CCCTCAAGCT                    20